United States Patent
Murray (10) Patent No.: US 10,761,038 B2
(45) Date of Patent: Sep. 1, 2020

(54) MULTI-ENERGY X-RAY ABSORPTION IMAGING FOR DETECTING FOREIGN OBJECTS ON A CONVEYOR

(71) Applicant: Laitram, L.L.C.

(72) Inventor: William S. Murray, New Orleans, LA (US)

(73) Assignee: Laitram, L.L.C., Harahan, LA (US)

( * ) Notice: Subject to any disclaimer, the term of this patent is extended or adjusted under 35 U.S.C. 154(b) by 0 days.

(21) Appl. No.: 16/346,823

(22) PCT Filed: Oct. 24, 2017

(86) PCT No.: PCT/US2017/058025
§ 371 (c)(1),
(2) Date: May 1, 2019

(87) PCT Pub. No.: WO2018/102051
PCT Pub. Date: Jun. 7, 2018

(65) Prior Publication Data
US 2019/0257773 A1   Aug. 22, 2019

Related U.S. Application Data

(60) Provisional application No. 62/427,423, filed on Nov. 29, 2016.

(51) Int. Cl.
*G01N 23/18*   (2018.01)
*G01N 23/04*   (2018.01)
*G01N 23/083*  (2018.01)

(52) U.S. Cl.
CPC .............. *G01N 23/18* (2013.01); *G01N 23/04* (2013.01); *G01N 23/083* (2013.01); *G01N 2223/423* (2013.01); *G01N 2223/643* (2013.01)

(58) Field of Classification Search
CPC .. G01N 23/18; G01N 33/02; G01N 2223/423; G01N 2223/643; G01N 23/04; G01N 23/083
See application file for complete search history.

(56) References Cited

U.S. PATENT DOCUMENTS 6,370,223 B1   4/2002   Gleason et al.
6,449,334 B1   9/2002   Mazess
(Continued)

FOREIGN PATENT DOCUMENTS

EP   2435344 B1   10/2014
EP   3078944 A1   10/2016
(Continued)

OTHER PUBLICATIONS

Matthew D. Wilson et al: "Multiple Module Pixellated CdTe Spectroscopic X-Ray Detector", IEEE Transactions on Nuclear Science, IEEE Service Center, New York, NY, US, vol. 60, No. 2, Apr. 1, 2013 (Apr. 1, 2013), pp. 1197-1200, XP011499742, ISSN: 0018-9499, DOI: 10.1109/TNS.2013.2240694.
(Continued)

*Primary Examiner* — Chih-Cheng Kao
(74) *Attorney, Agent, or Firm* — James T. Cronvich (57) ABSTRACT

Apparatus and method for detecting materials on a conveyor belt using multi-energy x-ray absorption imaging. A spectroscopic x-ray detector consisting of a line array of pixels receives x-rays from an x-ray source directed through the conveyor belt. The x-rays are attenuated as they pass through the belt and materials on the belt. The pixels each produce an energy spectrum of the received x-rays. The received energy spectrum of each pixel is related to the source x-ray spectrum to determine a measured attenuation, which is then related to an attenuation model that includes the attenuation coefficients of a set of preselected constituent materials expected to be in or on the belt. Mathematical
(Continued)

regression is used to fit the measured attenuation to the attenuation model to find the thickness of each constituent material for each pixel.

22 Claims, 4 Drawing Sheets

(56) References Cited

U.S. PATENT DOCUMENTS

| | | |
|---|---|---|
| 6,587,575 B1 | 7/2003 | Windham et al. |
| 7,480,363 B2 | 1/2009 | Lasiuk et al. |
| 8,068,656 B2 | 11/2011 | Hirose |
| 8,233,588 B2 | 7/2012 | Gibson et al. |
| 9,095,146 B2 | 8/2015 | Sigurdsson et al. |
| 9,410,888 B2 | 8/2016 | Jayasooriya |
| 9,448,326 B2 | 9/2016 | Radley et al. |
| 9,474,813 B2 | 10/2016 | Krueger |
| 9,888,894 B2 | 2/2018 | Wiedmann et al. |
| 2003/0147489 A1* | 8/2003 | Bijjani ............... G01N 23/046 378/4 |
| 2007/0291896 A1* | 12/2007 | Parham ............... G01N 23/046 378/37 |
| 2009/0316857 A1 | 12/2009 | David et al. |
| 2010/0220835 A1 | 9/2010 | Gibson et al. |
| 2011/0019797 A1 | 1/2011 | Morton |
| 2017/0269257 A1* | 9/2017 | Scoullar ............... G01V 5/0041 |

FOREIGN PATENT DOCUMENTS

| | | |
|---|---|---|
| JP | 2014109524 A | 6/2014 |
| WO | 2016171186 A1 | 10/2016 |

OTHER PUBLICATIONS

Lisa Lupo: "Foreign Object Detection", Dec. 11, 2014 (Dec. 11, 2014), XP055707851, Retrieved from the Internet: URL:https://www.qualityassurancemag.com//article/qa1214-foreign-object-detection-technology/[retrieved on Jun. 23, 2020].

Extended European Search Report of the European Patent Office, European Application No. 17876478.3, dated Jul. 20, 2020, European Patent Office, Munich, Germany.

* cited by examiner

MULTI-ENERGY X-RAY ABSORPTION IMAGING FOR DETECTING FOREIGN OBJECTS ON A CONVEYOR

BACKGROUND

The invention relates generally to x-ray systems and particularly to apparatus and methods for absorption imaging of product advancing continuously on a conveyor belt.

Damage to modular plastic conveyor belts used in the meat, poultry, and other food industries often causes shards of plastic to contaminate the conveyed product. Besides the costs of belt repair or replacement and interruption in production, the food processor must also deal with possible contamination of the conveyed food product by the shards.

SUMMARY

One version of apparatus for detecting materials on a conveyor belt comprises a conveyor belt conveying product in a conveying direction, an x-ray source, and a spectroscopic x-ray detector. The x-ray source directs a beam of x-rays having a source intensity distributed across a source spectrum through the thickness of the conveyor belt along an x-ray path. The spectroscopic x-ray detector comprises one or more pixels on the opposite side of the conveyor belt from the x-ray source that receive the x-rays that are attenuated as they pass through the conveyor belt, the conveyed product, and any foreign object advancing with the conveyed product on the conveyor belt at discrete pixel positions across the width of the conveyor belt. The one or more pixels define a corresponding field of view at each pixel position and determine a received intensity distributed across a received spectrum of the attenuated x-rays in its corresponding field of view at each pixel position. A processing system relates the received spectrum at each pixel position to the source spectrum to determine a measured attenuation of the x-rays and relates the measured attenuation to an x-ray attenuation model that includes attenuation coefficients of a set of preselected constituent materials including materials constituting the product, materials constituting the conveyor belt, and materials constituting foreign objects suspected as possible contaminants to determine the thickness of those materials in the fields of view at each pixel position.

One version of a method for detecting materials on a conveyor belt comprises:
(a) conveying product on a conveying surface in a conveying direction; (b) directing source x-rays having a source intensity distributed across a source x-ray spectrum along an x-ray path through the conveying surface and the product along a line across the width of the conveying surface; (c) detecting the x-rays attenuated on passing through the conveying surface at a plurality of pixel positions along the line with a spectroscopic x-ray detector comprising one or more pixels; (d) measuring the intensity of the attenuated x-rays in contiguous energy bins at each of the pixel positions to produce a received x-ray spectrum at each of the pixel positions; (e) relating the received x-ray spectrum to the source x-ray spectrum to determine a measured x-ray attenuation; and (f) relating the measured x-ray attenuation to an x-ray attenuation model that includes attenuation coefficients of a set of preselected constituent materials including materials constituting the product, materials constituting the conveyor belt, and materials constituting foreign objects suspected as possible contaminants to determine the thickness of those materials in the fields of view of each pixel in the line.

DETAILED DESCRIPTION

Figure 1:
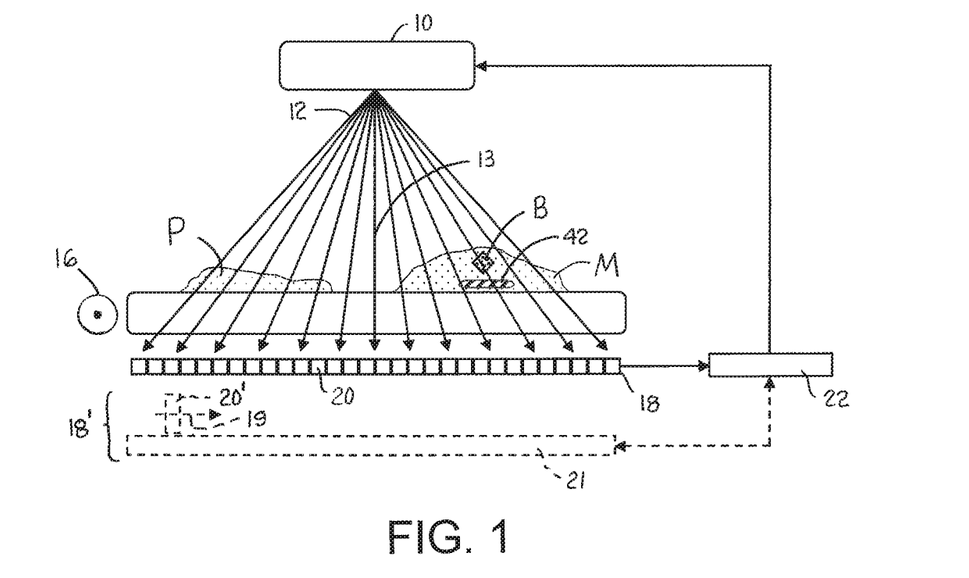
FIG. 1 is a schematic drawing of an x-ray imaging apparatus embodying features of the invention.

One version of an x-ray imaging apparatus embodying features of the invention is shown in FIG. 1. An x-ray source 10 generates a bremsstrahlung beam 12 of x-ray photons having a source intensity distributed over a broad source spectrum. The x-ray source directs the beam of x-rays in a fan beam along an x-ray path 13 through a conveyor belt 14 in a line across the width of the belt. One example of an x-ray source is an x-ray tube with a tungsten target. The conveyor belt advances with product P in a conveying direction 16 out of the page in FIG. 1. The x-rays 12 are attenuated by absorption as they pass through the conveyed product P and the conveyor belt 14. The attenuation depends on the thickness of the intervening material through which the x-rays pass from source to detector and on the attenuation coefficients of the various materials constituting the conveyor belt 14, the product P, and any other material that intersects the x-ray path 13. Spherical spreading of the x-rays along the x-ray path 13 also attenuates the x-ray intensity according to the inverse-square law, but that attenuation is set by the fixed distance between the x-ray source 10 and the detector 18 and so is known a priori and can be accounted for. The attenuated x-rays are received by a spectroscopic x-ray detector 18 on the opposite side of the conveyor belt 14 from the x-ray source 10.

The spectroscopic x-ray detector 18 comprises a linear array of individual static x-ray-detecting pixels 20 that extend across the width of the belt 14. As one example, the pixels 20 can be solid-state cadmium telluride (CdTe) detectors. Each pixel 20 produces a received energy spectrum binned in contiguous fixed-width bins, such as 1 keV-wide bins, at each pixel position across the width of the belt 14. Thus, the array of pixels 20 represents a line scan that measures the received x-ray intensity distributed across a received x-ray spectrum. The received x-ray spectra are sent to a processing system 22 that includes a programmable computer running software programs such as a two-dimensional (2D) imager, an x-ray source controller, and a user-interface controller. The x-ray source controller pulses the x-ray source 10 in synchrony with the sampling of the spectroscopic x-ray detector 18. An alternative x-ray detector 18', shown in dashed lines in FIG. 1, comprises a single x-ray-detecting pixel 20' that is advanced rapidly across the width of the belt 14 as indicated by arrow 19 by a driver, such as a stator 21 forming a linear synchronous motor with a magnetic forcer in the pixel 20'. The pixel 20' advances rapidly across the width of the belt 14 as it samples the received x-ray intensity at discrete pixel positions and measures the energy spectrum at those positions across the belt width, such as the positions defined by the pixels 20 in the fixed-array x-ray detector 18. As another alternative, an array of multiple pixels spaced apart at regular intervals across the belt width could be advanced by a driver over just the regular interval rather than the entire width of the belt 14 to measure the spectra at the pixel positions. The processing system 22 receives the pixel spectra and controls the operation of the pixel driver 21 in the moving-pixel detectors.

Figure 2:
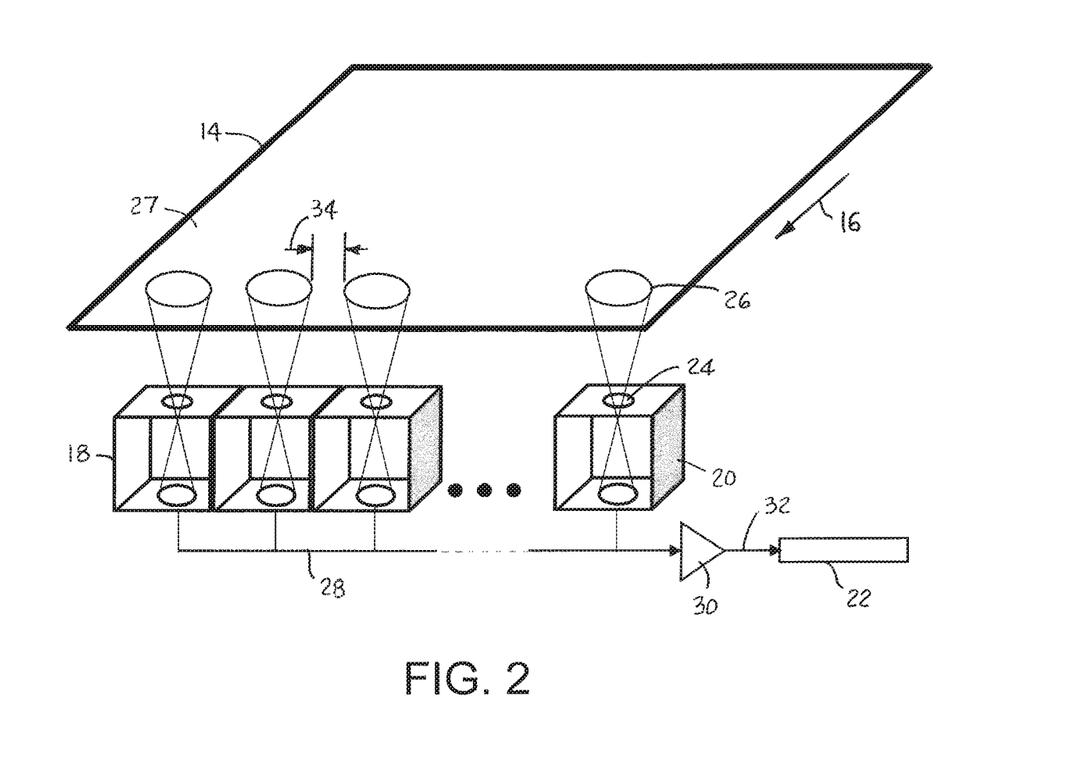
FIG. 2 is an enlarged view of a portion of the imaging apparatus of FIG. 1 illustrating the fields of view of a spectroscopic x-ray detector.

As shown in FIG. 2, each pixel 20 has a collimator 24 defining a field of view 26 at each pixel position that intersects the conveyor belt 14 at its conveying surface 27 and eliminates scatter. The output signals of the pixels 20 are sent over signal lines 28 to signal-conditioning circuits 30 including buffers and analog-to-digital converters (ADCs). Digital signals representing the received spectra are sent from the ADCs to the processing system 22 over digital lines 32. The distance 34 between laterally consecutive fields of view 26 is not greater than a predetermined detection threshold, i.e., the dimension of the smallest foreign object to be detected.

Figure 4:
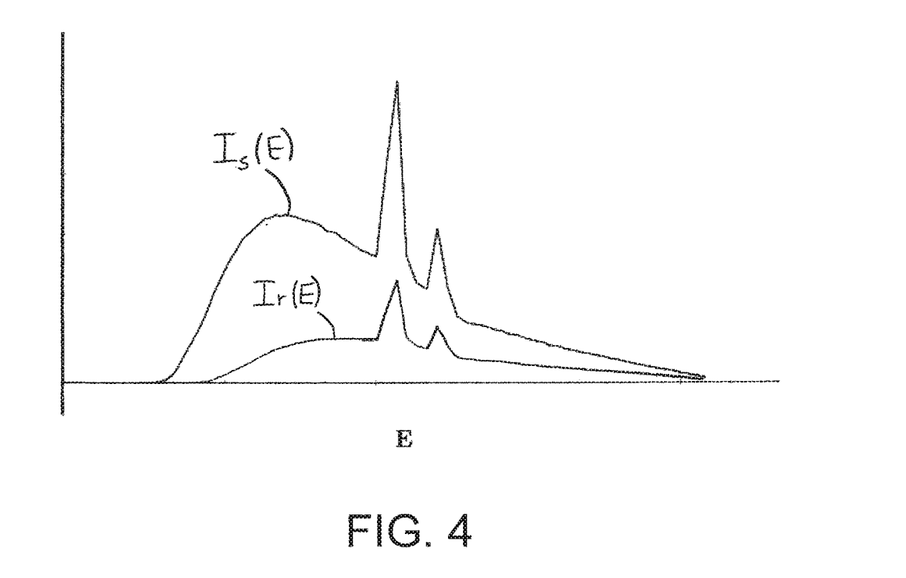
FIG. 4 is a graphical representation of exemplary energy spectra of x-rays emitted by an x-ray source and of x-rays received by the spectroscopic x-ray detector of FIG. 3 after attenuation.

The received x-ray spectrum at every pixel position is fitted to an x-ray attenuation model based on the Beer-Lambert Law, which models the received x-ray intensity $I_r$ in each energy bin at the pixel position as the product of the source x-ray intensity $I_s$ and an exponentially decaying term: $I_r(E) = I_s(E) \cdot e^{-\Sigma i [\mu(E) \cdot d]_i}$, where $I_r$ and $I_s$ are functions of the energy-bin centers E and $[\mu(E) \cdot d]_i$ is the attenuation along the x-ray path due to absorption by an ith preselected constituent material included in the attenuation model. FIG. 4 shows an example of the source x-ray spectrum for a tungsten x-ray tube and the attenuated received x-ray spectrum.

Figure 3:
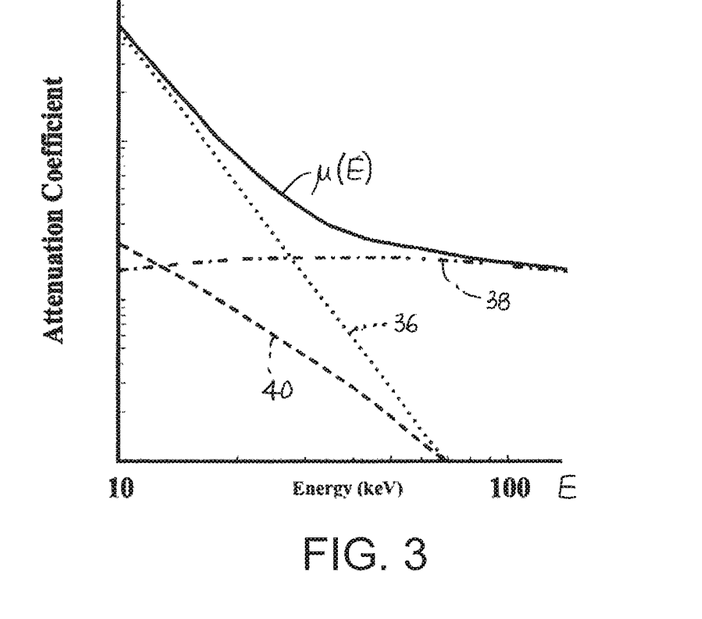
FIG. 3 is a log-log graph of the x-ray attenuation coefficients of an exemplary material as a function of x-ray energy level.
Figure 6:
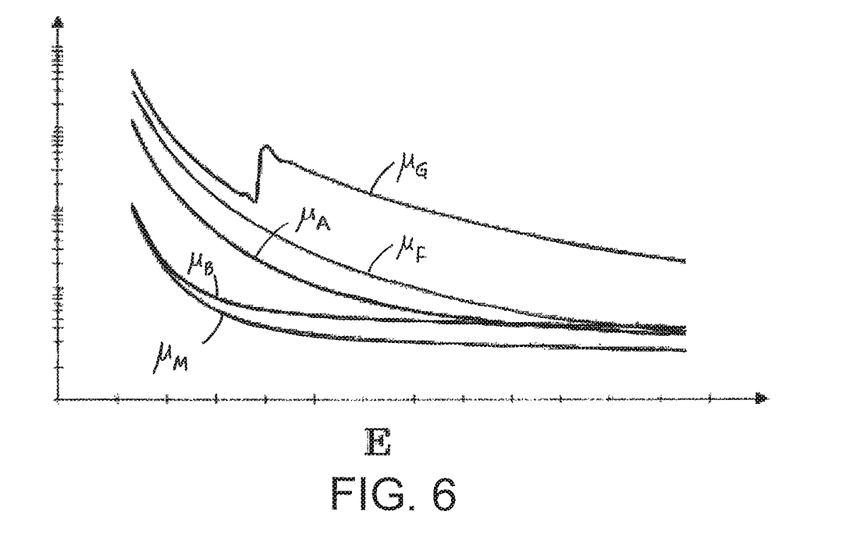
FIG. 6 is a semilog graph of the x-ray attenuation coefficients of various materials as a function of x-ray energy level.

As shown in FIG. 3, radiation interacts with matter in three ways: (1) the photoelectric effect 36, (2) Compton scattering 38, and (3) coherent scattering 40. The attenuation resulting from each of these effects for an exemplary material is a function of the x-ray energy E. The total attenuation coefficient $\mu(E)$ is the sum of the attenuations due to the three effects as a function of the energy E. As shown, $\mu$ decreases monotonically with increasing energy E for this exemplary material. FIG. 6 shows the relative attenuation coefficients of meat ($\mu_M$), bone ($\mu_B$), acetal ($\mu_A$), steel ($\mu_F$), and glass ($\mu_G$). As FIG. 6 clearly shows, glass has an attenuation coefficient that does not decrease monotonically with increasing energy. The attenuation coefficient $\mu(E)$—more strictly an attenuation function—is stored in tabular form in the processing system's memory or is computed algorithmically for each preselected constituent material of interest, i.e., those materials expected to be present: conveyor belt material; meat or other food product being conveyed; and the material constituting any other foreign object to be detected, such as a contaminant.

The attenuation model is represented by a system of equations given in matrix form as:

$$\begin{bmatrix} \mu_{1E_0} & \cdots & \mu_{NE_0} \\ \vdots & \ddots & \vdots \\ \mu_{1E_n} & \cdots & \mu_{NE_n} \end{bmatrix} \begin{bmatrix} d_1 \\ \vdots \\ d_N \end{bmatrix} = \begin{bmatrix} -\ln\left(\frac{I_r}{I_s}\right)E_0 \\ \vdots \\ -\ln\left(\frac{I_r}{I_s}\right)E_n \end{bmatrix},$$

where n is the number of energy bins used in the attenuation model; N is the number of preselected constituent materials in the attenuation model; $\mu_i(E_j)$ is the attenuation coefficient of preselected constituent material i in energy bin j; and $d_i$ is the thickness of preselected constituent material i. All the $\mu_i(E_j)$ attenuation coefficients are known and stored in the processing system's memory or calculated algorithmically by the processing system. Likewise, the source intensity ME)) is known for each energy bin $E_j$. The received intensity $I_r(E_j)$ for each energy bin is measured by the spectroscopic x-ray detector each sample time. The ratio of the received intensity to the source intensity is the measured attenuation. The processing system solves the system of equations by regression to determine the thicknesses di of each of the preselected constituent materials. The processing system uses a nonlinear regression, such as a least-squares regression. The Levenberg-Marquardt algorithm is one example of such a regression. The regression finds the best fit of the data to the attenuation model by minimizing the residuals of the di material thickness terms. The resulting di terms define the thickness of each of the preselected constituent materials for each pixel and, together with the calculated thicknesses for other samples, represent an image of the conveyor belt and the product and any other of the preselected constituent materials on the conveyor belt.

For example, to detect shards 42 of a conveyor belt 14 contaminating a piece of meat M as in FIG. 1, the preselected constituent materials might be: (a) acetal (the conveyor belt material); (b) muscle (a product constituent); and (c) bone B (a product constituent). The system of equations for each pixel position would include the known attenuation coefficients for each of the three materials (N=3). Because three independent equations suffice to solve for three unknowns (the thickness of each of the three materials), solving the equations for only three selected energy bins is all that is algebraically necessary to find the three thicknesses. But performing the regression on the attenuation equations for more than three bins provides, in most cases, a more robust solution. Once the thicknesses of the three preselected constituent materials are calculated, the calculated thickness of the acetal material is compared to the known thickness of the conveyor belt. If the calculated thickness is greater than the thickness of the belt 14, then a contaminating shard 42 of the acetal belt material is known to be present in the pixel's field of view. If additional potentially contaminating materials, such as glass, wood, and steel, are expected to possibly be present, their x-ray attenuation factors $\mu$ can be added to the attenuation model to detect their thicknesses.

Figure 5:
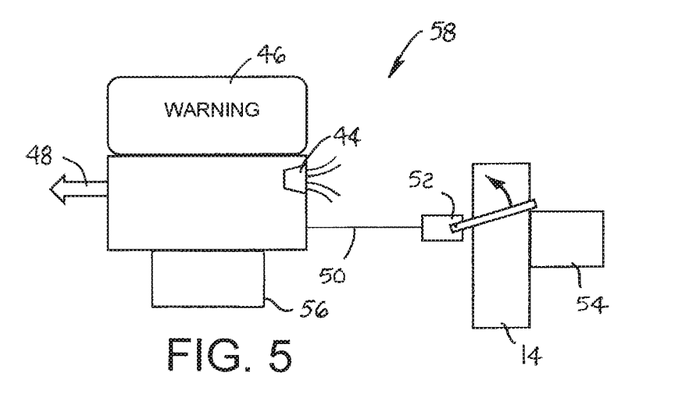
FIG. 5 is a schematic of a processing system for an x-ray imaging system as in FIG. 1 showing various notification options.

As shown in FIG. 5, once the processing system 22 determines that a contaminant is present, its user-interface controller can sound an alarm 44, display an alarm condition on a monitor 46, send an alarm message to other locations over a hardwired or wireless network 48, or issue a divert signal 50 to a diverter 52 to divert a portion of product from the conveyor belt 14 to a reject conveyor 54, stop the conveyor, or take any other action required to ensure that the contaminated product is removed from the conveyor line.

As previously described in reference to FIG. 2, the distance 34 between consecutive fields of view 26 sets the detection threshold in the width direction of the conveyor belt 14. The detection threshold in the conveying direction is set by the product of the belt speed and the detector sampling interval. So the sampling rate must be high enough that the length of conveyor belt that passes the detector line from sample to sample does not exceed the detection threshold, i.e., the dimension in the conveyor direction of the smallest contaminant to be detected. The processing system can determine sizes of contaminants and product by analyzing the results of product thicknesses at contiguous pixel positions and on consecutive samples. With a table of densities of the preselected constituent materials, the processing system can estimate weights. And because the attenuation of the x-rays is set by the net thickness of each of the materials in the x-ray path, the order of the materials along the path does not usually matter unless x-ray scattering by one or more of the materials is too great.

Figure 7:
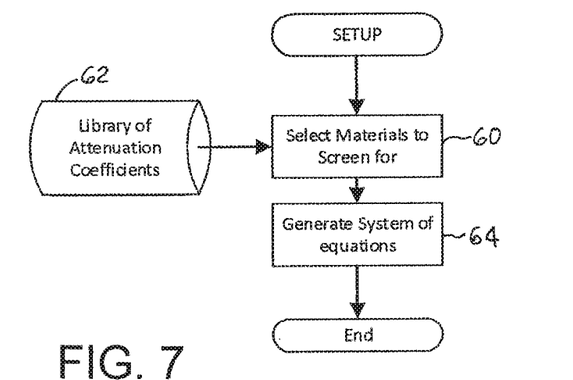
FIG. 7 is a flowchart of the setting up of the model of the constituent materials to be imaged by the x-ray imaging apparatus of FIG. 1.
Figure 8:
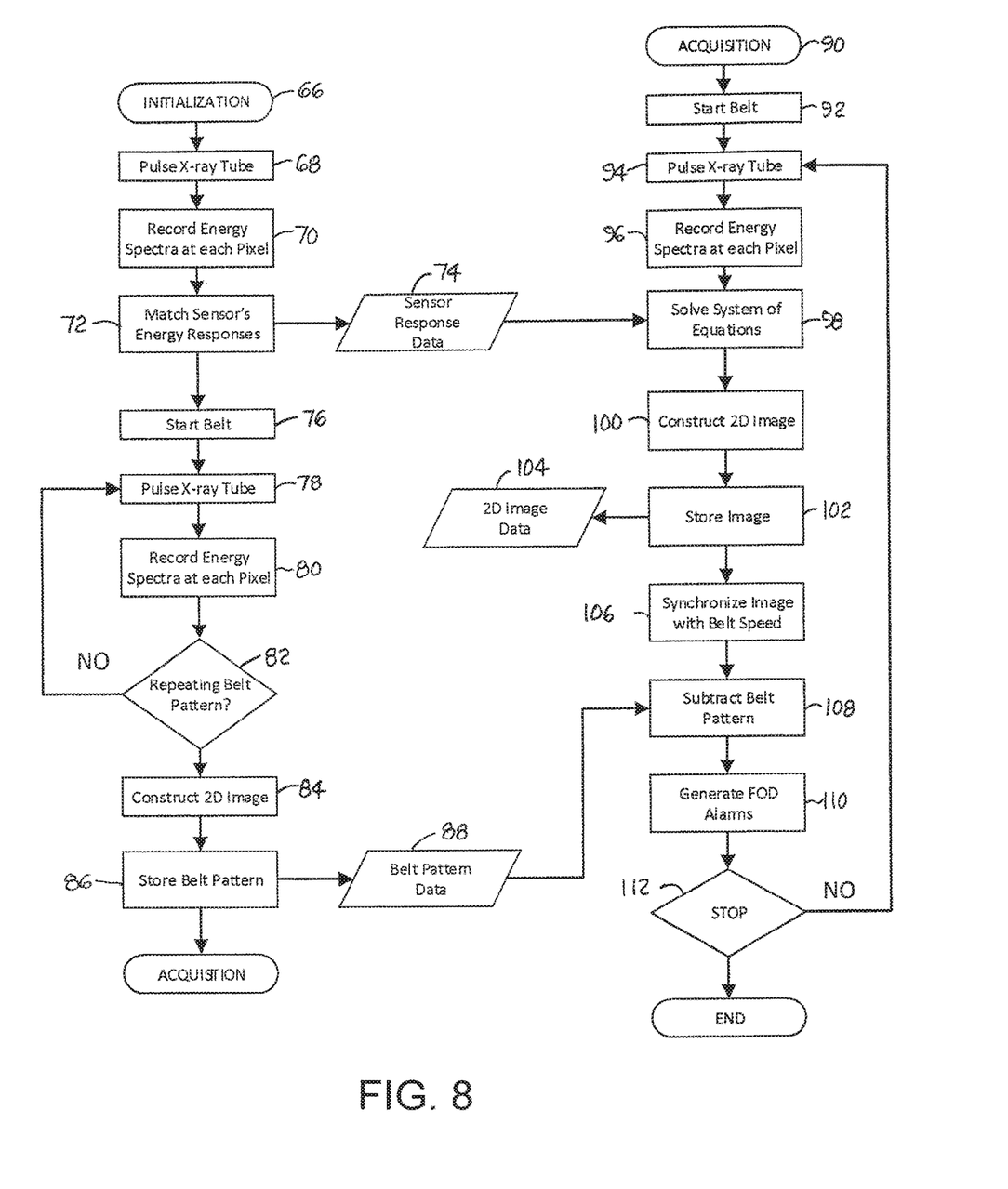
FIG. 8 is a flowchart of an exemplary process for imaging with the x-ray imaging apparatus of FIG. 1.

FIGS. 7 and 8 are flowcharts illustrating one method of detecting materials by the x-ray imaging system of FIG. 1. FIG. 8 is a flowchart of an exemplary process stored in program memory and executed by the processing system to generate the system of equations that constitute the attenuation model. The equations are set up by first, at step 60, selecting the constituent materials to be screened. The selection can be a fixed preselection of one or more materials or can be made by an operator over a user-interface device 56 in the user interface 58 (FIG. 5). The attenuation coefficients $\mu_i(E_j)$ for the selected materials are imported from a library 62 of attenuation coefficients for a variety of materials stored in the processing system's memory. Or they can be manually entered from the user input device 56. The processing system then generates the system of equations with the attenuation coefficients $\mu_i(E_j)$ of the selected materials at step 64 to construct the model.

The flowchart of FIG. 8 shows one version of a method executed by the processing system to detect suspected foreign objects on a conveyor belt. The first process (initialization 66) constructs a 2D image of an empty conveyor belt or conveyor-belt segment devoid of product. In the case of a belt with a regularly repeating belt pattern, as in most modular conveyor belts, a 2D image of a single belt row may suffice to define the entire belt. The processing system first pulses the x-ray source at step 68 and then records the received energy spectrum for each pixel position at step 70. The responses of the x-ray detector to the empty belt are used to compute calibration terms used to match the spectra bin-to-bin across the width of the belt so that all spectra are identical at step 72. The calibration terms are stored 74 in the processing system's memory for use in adjusting all the measured spectra to match. The initialization process then signals the belt motor to drive the conveyor belt at a constant speed at step 76. The x-ray source is pulsed at x-ray source controller step 78, and the received x-ray spectrum at each pixel position is measured and recorded at step 80 to produce a line scan. The process of pulsing the x-ray source 78 and recording the spectra 80 is repeated at a fixed pulse and sample rate to build up consecutive line scans until a repeating belt pattern is detected as indicated by step 82. If the belt is, for example, a flat belt of uniform thickness and construction with no repeating pattern, a uniform pattern can be used. The frame of line-scan spectra representing the repeating empty belt pattern is used to construct a 2D image of the pattern at step 84. The belt pattern is stored at step 86 for use 88 in the detection of foreign objects on the belt. The initialization process 66 can be run periodically to recalibrate the x-ray detector and to account for changes in the belt due to wear or module replacement.

With the x-ray detector calibrated and the belt pattern saved, the processing system runs the acquisition process 90 on the conveyor belt running loaded with product. The process first starts the conveyor belt at step 92 and pulses the x-ray source at step 94. The energy spectrum at each pixel position is recorded at step 96. The system of equations representing the attenuation model for the selected constituent materials is solved for a line scan after the calibration terms 74 are applied to the energy spectra at step 98 to construct a 2D image of a frame consisting of consecutive line images at step 100. The 2D image is stored at step 102. The stored 2D image 104 is available for display. If the belt speed has changed from the time when the empty belt pattern was stored by the initialization process 66, the frame image of the loaded belt is adjusted to match the frame length of the stored belt pattern or vice versa. And the loaded belt frame is synchronized, or aligned, with the empty belt pattern. Once that is done at step 106, the belt-pattern frame is subtracted from the loaded belt frame at step 108. The resulting difference provides the thicknesses of each of the preselected constituent materials at each pixel position in the frame. If any of the thicknesses exceeds an alarm threshold, a foreign-object-detection (FOD) alarm is sounded or other action is taken at step 110. If the belt is stopped at step 112, the acquisition process is exited. If the belt continues running, the process resumes in a regular repetitive fashion by pulsing the x-ray source again at step 94.

Although the processing system's initialization 66 and acquisition 90 processes can be implemented to run as individual sequential processes with program loops and delays to achieve the proper timing, the processes can alternatively be implemented more consistent with realtime multi-tasking programming using interrupt service routines and a task manager routine. As just one example, in the case of the acquisition process, the periodic pulsing of the x-ray source 94 and recording of the received energy spectra 96 could be implemented as an interrupt-service routine (ISR) scheduled to run at a preselected sampling rate. After all the spectra are recorded, the ISR could then bid the 2D imager task scheduled by the task manager to solve the system of equations 98, construct the 2D image 100, and store it 102 so that it can be displayed by a user-interface controller task. The 2D imager task could also synchronize the image with belt speed 106, subtract the stored empty belt pattern from the computed image 108, and generate FOD alarms 110. But those steps could alternatively be run in a separate task bid to run upon construction of the 2D image.

Although the attenuation model was described as using fixed-width energy bins, it is possible to combine energy bins to form effectively wider energy bins than those automatically produced by the pixels. Because the attenuation of x-rays is greater at lower energy levels, the pixels' energy bins at lower energy levels could be combined to form wider energy bins to be used in the attenuation model. At the higher energies, the energy bins used in the system of equations need not be as wide as those at the lower energies. But because the attenuation curve is much steeper at low energies, wider bins increase the error in the estimates of the attenuation values to be assigned to wide low-energy bins. To maintain the stability of the regression solution of the attenuation model, the widths of the bins are optimized so that the error term due to statistics (i.e., the count rate in an energy bin) and the estimation error in attenuation coefficient due to the steepness of the curve are approximately equal in magnitude.

Although the x-ray imaging apparatus has been described mainly in reference to detecting contaminants, especially shards of conveyor belt, it can also be used to detect belt features, such as thickened portions of the belt, which the processing system could use as positional references to measure belt elongation or belt speed or to determine the location of contaminants on the belt. And if a longitudinal lane of the belt is maintained clear of product, pixels under that lane could be used to measure the source x-ray intensity and spectrum in real time.

What is claimed is:

1. Apparatus for detecting materials on a conveyor belt, comprising:
    a conveyor belt conveying product in a conveying direction;
    an x-ray source directing a beam of x-rays having a source intensity distributed across a source spectrum through the thickness of the conveyor belt along an x-ray path;
    a spectroscopic x-ray detector comprising one or more pixels on the opposite side of the conveyor belt from the x-ray source that receive the x-rays that are attenuated as they pass through the conveyor belt, the conveyed product, and any foreign object advancing with the conveyed product on the conveyor belt at discrete pixel positions across the width of the conveyor belt;
    wherein the one or more pixels define a corresponding field of view at each pixel position and determine a received intensity distributed across a received spectrum of the attenuated x-rays in its corresponding field of view at each pixel position;
    a processing system that relates the received spectrum at each pixel position to the source spectrum to determine a measured attenuation of the x-rays and relates the measured attenuation to an x-ray attenuation model that includes attenuation coefficients of a set of preselected constituent materials including materials constituting the product, materials constituting the conveyor belt, and materials constituting foreign objects suspected as possible contaminants to determine the thickness of those materials in the fields of view at each pixel position.

2. Apparatus as in claim 1 wherein the x-ray attenuation model follows the Beer-Lambert Law.

3. Apparatus as in claim 1 wherein the received spectrum at each pixel position is binned in contiguous energy bins and wherein the processing system defines a system of attenuation equations relating the ratio of the received intensity to the source intensity in preselected energy bins to the x-ray attenuation model for the selected energy bins to determine the thickness along the x-ray path of each of the preselected constituent materials.

4. Apparatus as in claim 3 wherein the preselected energy bins comprise some or all of the energy bins.

5. Apparatus as in claim 3 wherein the number of preselected energy bins is greater than or equal to the number of preselected constituent materials.

6. Apparatus as in claim 3 wherein all the energy bins are the same width.

7. Apparatus as in claim 3 wherein the selected energy bins are wider at low energy levels than at high energy levels.

8. Apparatus as in claim 3 wherein the processing system performs a nonlinear regression on the system of equations to determine a best fit of the x-ray attenuation model to the ratios of the received intensity to the source intensity in each of the selected energy bins by minimizing the residual of the thicknesses along the x-ray path of each of the preselected constituent materials.

9. Apparatus as in claim 8 wherein the system of equations includes one equation for each of the preselected energy bins of the form $\Sigma_{i=1}^{N}\mu_i d_i = -\ln(I_r/I_s)$, where N is the number of preselected constituent materials in the x-ray attenuation model, $\mu_i$ is the attenuation coefficient of the ith preselected constituent material for the energy bin, $d_i$ is the thickness along the x-ray path of the ith preselected constituent material, $I_r$ is the received x-ray intensity in the energy bin, and $I_s$ is the source x-ray intensity in the energy bin.

10. Apparatus as in claim 1 wherein the spectroscopic x-ray detector comprises a single pixel or a plurality of spaced-apart pixels and a driver driving the single pixel or the plurality of spaced-apart pixels across the width of the conveyor belt to receive the x-rays at each pixel position.

11. Apparatus as in claim 1 wherein the processing system determines the thickness of the constituent material of the conveyor belt along the x-ray path for each of the pixel positions and compares that thickness to a predetermined thickness of the conveyor belt along the x-ray path and indicates the presence of a contaminating piece of conveyor belt material if the determined thickness of the constituent material of the conveyor belt exceeds the predetermined thickness of the conveyor belt.

12. Apparatus as in claim 1 wherein the processing system sounds an alarm, displays an alarm condition, sends an alarm message, or issues a divert signal to a diverter to divert a portion of product from the conveyor belt upon determining the presence of a contaminant on the conveyor belt.

13. Apparatus as in claim 1 wherein the processing system pulses the x-ray source on and the spectroscopic x-ray detector samples in synchrony at a rate high enough that the length of conveyor belt that passes the spectroscopic x-ray detector from sample to sample is not greater than a predetermined detection threshold of the contaminant.

14. Apparatus as in claim 1 wherein the corresponding fields of view at consecutive pixel positions are separated by a distance not greater than a predetermined detection threshold of the contaminant.

15. Apparatus as in claim 1 wherein the corresponding field of view of at least one of the one or more pixels is located at a position in a longitudinal lane of the conveyor belt that is maintained clear of product.

16. A method for detecting materials on a conveyor belt, comprising:
    conveying product on a conveying surface in a conveying direction;
    directing source x-rays having a source intensity distributed across a source x-ray spectrum along an x-ray path through the conveying surface and the product along a line across the width of the conveying surface;
    detecting the x-rays attenuated on passing through the conveying surface at a plurality of pixel positions along the line with a spectroscopic x-ray detector comprising one or more pixels;
    measuring the intensity of the attenuated x-rays in contiguous energy bins at each of the pixel positions to produce a received x-ray spectrum at each of the pixel positions;
    relating the received x-ray spectrum to the source x-ray spectrum to determine a measured x-ray attenuation;
    relating the measured x-ray attenuation to an x-ray attenuation model that includes attenuation coefficients of a set of preselected constituent materials including materials constituting the product, materials constituting the conveyor belt, and materials constituting foreign objects suspected as possible contaminants to determine the thickness of those materials in the fields of view of each pixel in the line.

17. The method of claim 16 comprising defining a system of attenuation equations under the attenuation model that relate the ratio of the received intensity to the source intensity in individual preselected energy bins to the x-ray attenuation model for each of the preselected energy bins to determine the thickness along the x-ray path of each of the constituent materials.

18. The method of claim 17 comprising performing a nonlinear regression on the system of equations to determine a best fit of the x-ray attenuation model to the ratios of the received intensity to the source intensity in each preselected energy bin by minimizing the residual of the thicknesses along the x-ray path of each of the preselected constituent materials.

19. The method of claim 16 comprising sounding an alarm, displaying an alarm condition, sending an alarm message, or issuing a divert signal to a diverter to divert a portion of product from the conveying surface upon determining the presence of a contaminant.

20. The method of claim 16 comprising selecting the attenuation coefficients of the set of preselected constituent materials from a library of attenuation coefficients of various materials.

21. The method of claim 16 comprising producing a two-dimensional image of the conveyor belt carrying product from the received spectrum at each pixel position for consecutive lines.

22. The method of claim 21 comprising first running the conveyor belt devoid of product and producing an empty belt pattern as a two-dimensional image of the conveyor belt devoid of product from the received spectrum at each pixel position for consecutive lines and subtracting the empty belt pattern from the two-dimensional image of the conveyor belt carrying product to determine the presence of the preselected materials not forming part of the conveyor belt.

* * * * *

UNITED STATES PATENT AND TRADEMARK OFFICE
CERTIFICATE OF CORRECTION

PATENT NO. : 10,761,038 B2
APPLICATION NO. : 16/346823
DATED : September 1, 2020
INVENTOR(S) : Murray Page 1 of 1

It is certified that error appears in the above-identified patent and that said Letters Patent is hereby corrected as shown below:

In the Specification

In Column 4, Line 17, replace "ME))" with --$I_s(E_j)$--

In Column 4, Line 22 and Line 28 (two places), replace "di" with --$d_i$--

Signed and Sealed this
Twenty-ninth Day of September, 2020

Andrei Iancu
*Director of the United States Patent and Trademark Office*